United States Patent [19]

Tsunekawa et al.

[11] 4,404,150
[45] Sep. 13, 1983

[54] CYCLIC PYROPHOSPHATE DERIVATIVES AND THEIR PREPARATION

[75] Inventors: Masayoshi Tsunekawa, Toyonaka; Nobuyoshi Miyoshi, Ibaraki; Tamotsu Komura, Nara, all of Japan

[73] Assignee: Sankin Industry Co., Ltd., Osaka, Japan

[21] Appl. No.: 231,914

[22] Filed: Feb. 5, 1981

[30] Foreign Application Priority Data

Aug. 20, 1980 [JP] Japan .................. 55-114995

[51] Int. Cl.$^3$ .............................. C07F 9/15
[52] U.S. Cl. .................. 260/927 R; 260/930; 260/988; 433/226
[58] Field of Search .................. 260/927 R, 988

[56] References Cited

U.S. PATENT DOCUMENTS 3,476,699 11/1969 Kauder et al. .................. 260/927 R

FOREIGN PATENT DOCUMENTS 2082184 3/1982 United Kingdom ............ 260/927 R

*Primary Examiner*—Anton H. Sutto
*Attorney, Agent, or Firm*—Oblon, Fisher, Spivak, McClelland & Maier

[57] ABSTRACT

A cyclic pyrophosphate derivative having the formula

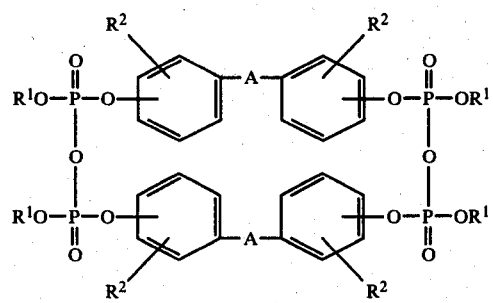

wherein A represents a direct bond between the two phenyl rings or a divalent moiety selected from the group consisting of lower alkylene, aryl substituted lower alkylene, cycloalkylidene, sulfonyl and oxy; $R^1$ represents alkyl, acryloyloxy lower alkyl or methacryloyloxy lower alkyl in which the lower alkyl can be substituted with halogen; and $R^2$ represents independently hydrogen, halogen, lower alkyl or lower alkoxy; a method of preparing the same, a dental filling material comprising the same and a method of filling dental cavities are disclosed.

17 Claims, No Drawings

CYCLIC PYROPHOSPHATE DERIVATIVES AND THEIR PREPARATION

BACKGROUND OF THE INVENTION

1. Field of the Invention

This invention relates to cyclic pyrophosphate derivatives, their process of preparation, a dental filling material composed of the same, and a dental filling technique making use of this material.

2. Description of the Prior Art

Many kinds of dental cements have been applied as dental filling materials. Recently, some monomers of methacrylate, as the resin-based filling material, have been given attention as well. One of the well-known monomers is a compound of the following formula (glycidyl methacrylate derivative of bisphenol A; Bis-GMA):

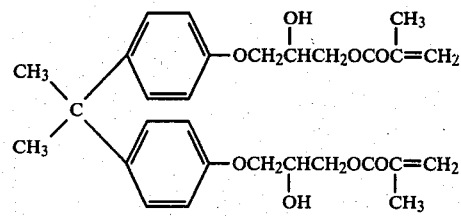

which is disclosed in U.S. Pat. Nos. 3,066,112 and 3,179,623. To this monomer are added the proper reactive diluents, such as methyl methacrylate, ethyleneglycol dimethacrylate, triethyleneglycol dimethacrylate or tetraethyleneglycol dimethacrylate, making the mixture less viscous and thereby suitable for practical use. For filling cavities of teeth, tert.-amines and peroxides are added to the mixture, which is then cured to serve as an excellent restorative material of higher mechanical properties.

The handling characteristics of this material are not very good, since Bis-GMA is extremely viscous absent a large quantity of diluent and sometimes tends to absorb undesirable amounts of water which causes trouble in that a less cured resin is obtained which has lower mechanical strength. Also, as a fundamental problem, the hardening time between gelatination and complete hardening is too long and patients are greatly discomfited waiting until the resin is completely cured.

Additionally, since the diluents described above are low molecular weight monomers which penetrate into pulpal tissues, they irritate the patient, and it would be desirable to reduce the amount of diluent as much as possible.

A need therefore continues to exist for a resin monomer which overcomes the above-mentioned difficulties and which can be completely polymerized in a short period of time without the necessity of adding low molecular weight diluents.

SUMMARY OF THE INVENTION

Accordingly, one object of the invention is to provide a resin monomer suitable for use in a dental filling material.

Another object of the invention is to provide an effective procedure for synthesis of the monomer.

Another object of the invention is to provide a dental filling material composed of this monomer.

A further object of the invention is to provide a dental technique for filling cavities with this material.

Briefly, these objects and other objects of the invention as hereinafter will become more readily apparent can be attained by providing cyclic pyrophosphate derivatives, which are polymerizable monomers, of the formula:

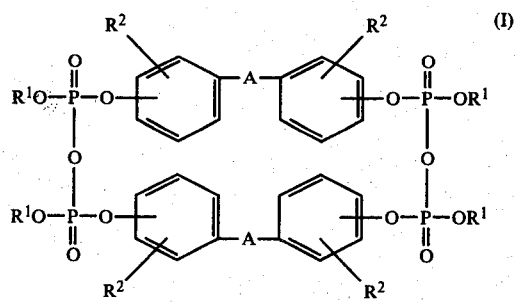

wherein A represents a direct bond between the two phenyl rings, thereby forming a biphenyl ring, or a divalent moiety selected from the group consisting of lower alkylene, aryl substituted lower alkylene, cycloalkylidene, sulfonyl and oxy;

$R^1$ represents allyl, acryloyloxy lower alkyl or methacryloyloxy lower alkyl, in which the lower alkyl can be substituted by halogen atoms; and $R^2$ represents independently hydrogen, halogen, lower alkyl or lower alkoxy.

DETAILED DESCRIPTION OF THE PREFERRED EMBODIMENTS

The compounds of this invention, as shown in Formula (I), can be prepared by the following reaction scheme, wherein A, $R^1$ and $R^2$ have the same meanings as set forth above, and X is halogen.

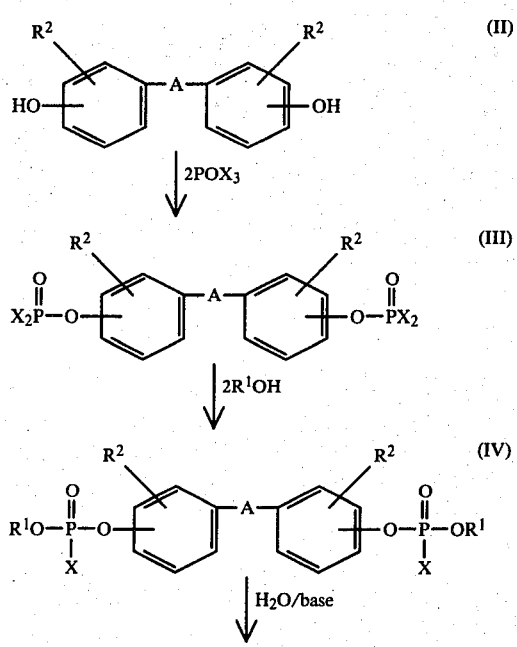

-continued

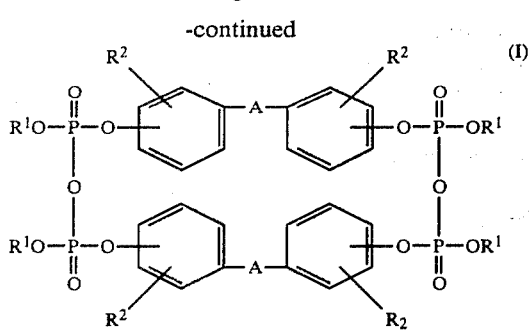

The reaction mechanism in the formation of the compounds of this invention (I) from compound (IV) is though to proceed via the formation of an intermediate (V), which is formed by hydrolysis of a portion of the compound (IV); the intermediate (V) then reacting with the unhydrolyzed compound (IV) in the presence of the base (a dehydrohalogenating agent) to produce the compound (I) of this invention. A description of the mechanism is as follows, wherein A, $R^1$, $R^2$ and X have the same meanings as set forth above.

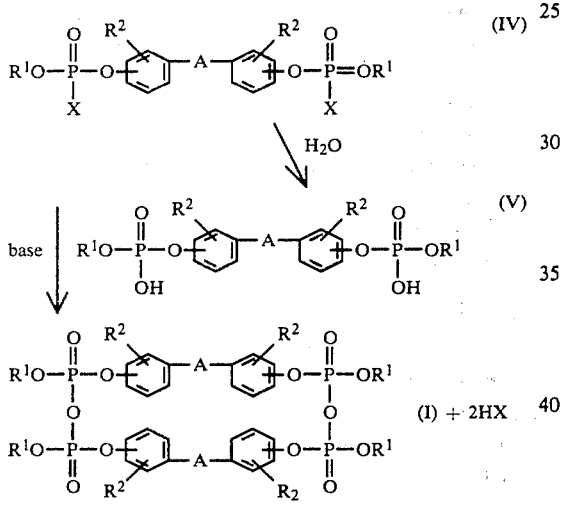

According to the present invention, A may represent a direct bond between the two phenyl rings, thereby forming a biphenyl ring, or a divalent moiety selected from the group consisting of lower alkylene, aryl substituted lower alkylene, cycloalkylidene, sulfonyl and oxy.

The lower alkylene moiety includes those members having one to six carbon atoms, such as methylene, ethylene, trimethylene, propylene, dimethyl methylene, tetramethylene, ethylethylene, 2-methyl trimethylene, pentamethylene, 2-ethyl trimethylene, 2,2-dimethyl trimethylene, 1,3-dimethyl trimethylene, 1-ethyl trimethylene and hexamethylene.

The aryl substituted lower alkylene moiety includes the lower alkylene, as described above, which have been substituted with phenyl, α-naphthyl, β-naphthyl or anthranyl groups. The number of aryl substituents is not critical, being limited only by the number of available sites for substitution and well-known steric hindrances.

The aryl group may be unsubstituted or substituted by lower alkyl, lower alkoxy and halogen. Suitable lower alkyl groups include those containing one to six carbon atoms, such as methyl, ethyl, propyl, iso-propyl, butyl, tert-butyl, pentyl and hexyl. Suitable lower alkoxy groups include those containing one to six carbon atoms, such as methoxy, ethoxy, propoxy, iso-propoxy, butoxy, tert-butoxy, pentyloxy, and hexyloxy. Suitable halogen atoms include fluorine, chlorine, bromine and iodine.

The cycloalkylidene moiety includes cyclopentylidene and cyclohexylidene.

The group $R^1$ represents allyl, acryloyloxy lower alkyl and methacryloyloxy lower alkyl, wherein the vinyl group present in these moieties is the cause of the polymerizability of compound (I). The lower alkyl group in $R^1$ is the same as described above and, furthermore, may be substituted by halogen, such as fluorine, chlorine, bromine and iodine.

The group $R^2$, which is substituted at an arbitrary position of the phenyl ring, represents independently hydrogen, lower alkyl, lower alkoxy and halogen. The lower alkyl, lower alkoxy and halogen are the same as described above.

According to the present, the compounds (I) may be prepared by the following reaction sequence, which has been schematically illustrated above:

Compound (II)→Compound (III)

Under anhydrous conditions, compound (II) is reacted with a phosphoryl halide, which serves as both a reagent and solvent. Other solvents may be present, provided they are inert under the conditions of the reaction. The reaction temperature is not critical, however, reflux or heating can be used to ensure better completion of the reaction.

Compound (III)→Compound (IV)

Under anhydrous conditions, the alcohol $R^1OH$ ($R^1$ being defined as above) is reacted with compound (III). The reaction is preferably carried out in the presence of a solvent which does not hinder the reaction, such as methylene chloride or chloroform. The reaction temperature is not critical, however, due to its exothermic nature, cooling or operation at room temperature is recommended.

Compound (IV)→Compound (I)

This reaction involves the intermediate (V) and a sequential hydrolysis followed by dehydrohalogenation-condensation. For hydrolysis, water may merely be added to the reaction mixture, the reaction temperature not being critical. Dehydrohalogenation-condensation occurs in the presence of an organic or inorganic base, which is added to the reaction mixture while hydrolysis is proceeding. The hydrolyzed compound (IV) (intermediate (V)) reacting with the remaining unhydrolyzed comound (IV) to give compound (I). The nature of the added base is not critical, but, tert-amines, such as trialkyl amine or pyridine, are preferred as the organic base, and weak bases, such as carbonate, are preferred as the inorganic base.

Compound (I) obtained by the above-defined procedure is a polymerizable monomer by virtue of the vinyl group which can undergo addition polymerization. Polymerization can be effected by means of light, heat or ultraviolet lamp, as well as by the addition of an initiator and an accelerator. Peroxides, such as benzoic peroxide, can be utilized as the initiator, while amines can be used as the accelerator. No criticality resides in the selection of peroxides or amines, however, in regard to the use of compound (I) in a dental filling material, care should be taken to assure non-toxicity and rapid curing times.

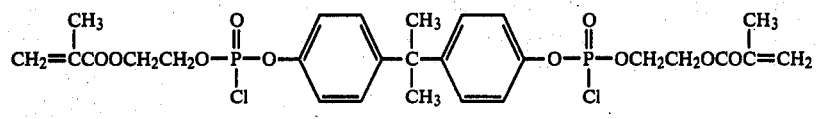

Though compound (I), per se, can be used as a dental filling material, conventional organic or inorganic fillers can be combined with compound (I) to produce compositions of higher strength. Additionally, being less viscous, less diluent, i.e. conventional reactive diluent, if so desired, can be used in formulating dental

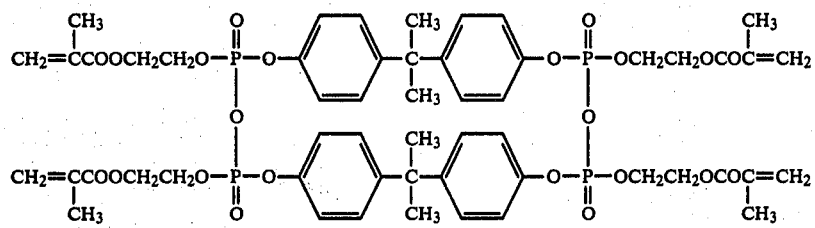

filling compositions, thereby lessening the irritation of pulpal tissues. Hardening time is also remarkably decreased so as to cause much less patient discomfiture.

Compound (I), after curing, gives a resin possessing excellent physical properties, such as compressive strength, hardness and anti-abrasion properties, suitable for industrial application as well as in dental filling materials.

Having generally described this invention, a further understanding can be obtained by reference to certain specific examples which are provided herein for purposes of illustration only and are not intended to be limiting unless otherwise specified.

EXAMPLE 1

A mixture of bis-phenol A (228 g), phosphoryl chloride (320 g) and calcium chloride (50 g) was heated at 150° C. for 5 hrs. After the reaction was over, the excess of phosphoryl chloride was distilled out under reduced pressure to give the following phosphoryl dichloride:

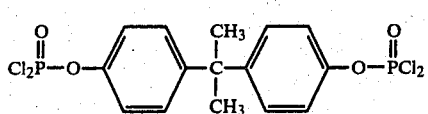

A solution of this phosphoryl dichloride in methylene chloride (500 ml) was added dropwise at 0° C. to a solution of 2-hydroxyethyl methacrylate (260 g) and pyridine (240 g) in methylene chloride (300 ml). The mixture was stirred for 2 hrs. to give the following phosphoryl chloride:

Cold water was then added and stirring continued for another 2 hrs. After hydrolysis was completed, the organic layer was washed with 5% hydrochloric acid, 5% sodium hydroxide solution and water, and then dried. Evaporation of the solvent gave the pyrophosphate (530 g) as a colorless oil:

IR: $\nu_{-max}$ cm$^{-1}$
2950, 1720, 1630, 1600, 1365, 1295, 980
NMR(CDCl$_3$): δ
7.14 (AB$_q$, 4H×4, arom. Protons)
6.10 (bs. 1H×4, vinyl Proton)
5.55 (m, 1H×4, vinyl Proton)
4.25 (m, 4H×4, —CH$_2$CH$_2$—)
1.90 (d, 3H×4, vinyl CH$_3$)
1.60 (m, 3H×4, —CH$_3$)

EXAMPLE 2

The phosphoryl dichloride (470 g), obtained by the same procedure as shown in Example 1, was reacted with 2-hydroxy propyl methacrylate (288 g) and pyridine (240 g), and treated by the same procedure as in Example 1 to give the following pyrophosphate (442 g):

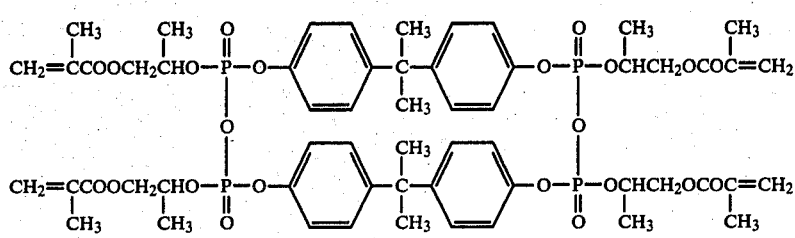

IR: $\nu_{max}$ cm$^{-1}$
2950, 1720, 1630, 1600, 1370, 1290, 990
NMR(CDCl$_3$): δ
7.14 (AB$_q$, 4H×4, arom, protons)
6.10 (bs, 1H×4, vinyl proton)
5.55 (m, 1H×4, vinyl proton)
4.85 (m, 1H×4, —CH$_2$C$\underline{H}$CH$_3$)
4.15 (m, 2H×4, —C$\underline{H_2}$CHCH$_2$)
1.90 (d, 3H×4, vinyl CH$_3$)
1.60 (m, 3H×4, —CH$_3$)
1.30 (m, 3H×4, —CH$_2$CHC$\underline{H_3}$)

EXAMPLE 3

3-chloro-4,4'-dihydroxy biphenyl (324 g), phosphoryl chloride (320 g) and calcium chloride (50 g) were reacted in the same manner as shown in Example 1 to give the following phosphoryl dichloride (550 g):

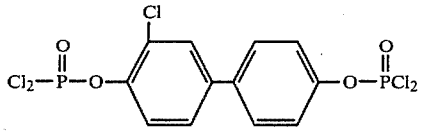

The phosphoryl dichloride was reacted with 2-hydroxyethyl acrylate (220 g) and pyridine (240 g), and treated in the same manner as in Example 1 to give the pyrophosphate (415 g):

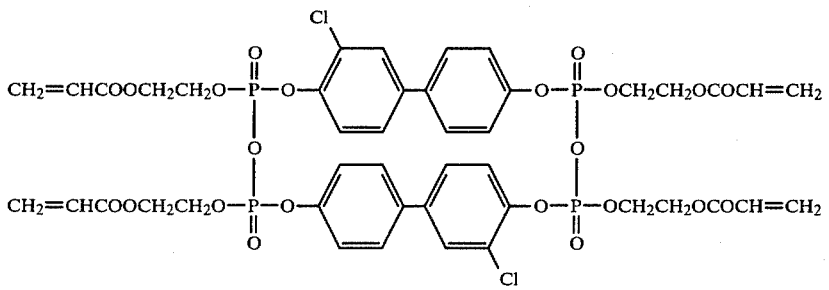

IR: $\nu_{max}\,\text{cm}^{-1}$
2950, 1720, 1630, 1600, 1365, 1295, 980, 845
NMR(CDCl$_3$): δ
  7.30 (m, 3H×2, arom. protons)
  7.20 (ABq, 4H×2, arom. protons)
  6.35 (m, 3H×4, vinyl protons)
  4.25 (m, 4H×4, —CH$_2$CH$_2$—)

EXAMPLE 4

Bis(4-hydroxyphenyl)phenylmethane (276 g), phosphoryl chloride (320 g) and calcium chloride (50 g) were reacted in the same manner as shown in Example 1 to give the following phosphoryl dichloride (503 g):

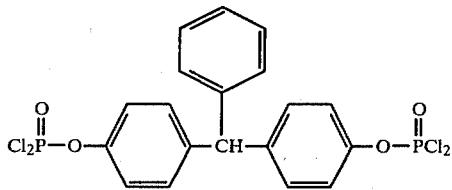

The phosphoryl dichloride was reacted with allyl alcohol (110 g) and pyridine (240 g), and treated in the same manner as in Example 1 to give the pyrophosphate (388 g):

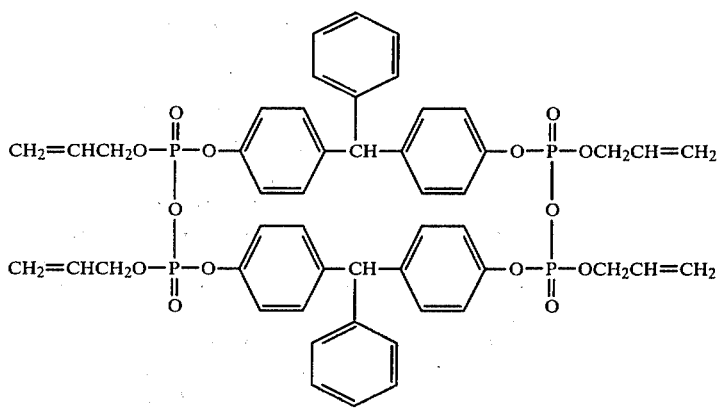

IR: $\nu_{max}\,\text{cm}^{-1}$
3050, 2900, 1630, 1600, 1365, 1295, 980
NMR(CDCl$_3$): δ
  7.20 (m, 13H×2, arom. protons)
  5.62 (m, 2H×4, vinyl protons)
  5.60 (s, 1H×2, —CH)
  4.10 (bs, 1H×4, vinyl proton)
  3.50 (t, 2H×4, —CH$_2$—)

EXAMPLE 5

Bis(2-hydroxy-5-chlorophenyl)methane (476 g), phosphoryl chloride (320 g) and calcium chloride (50 g) were reacted in the same manner as shown in Example 1 to give the following phosphoryl dichloride (680 g):

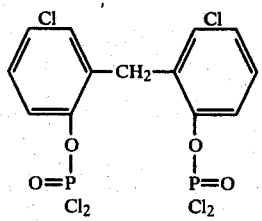

The phosphoryl dichloride was reacted with 2-hydroxyethyl methacrylate (240 g) and pyridine (240 g), and treated in the same manner as in Example 1 to give the pyrophosphate (710 g):

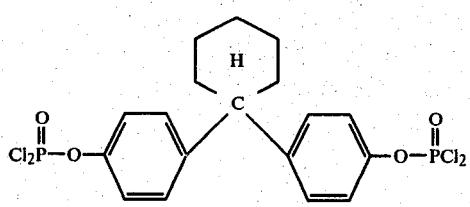

The phosphoryl dichloride was reacted with 2-hydroxyethyl methacrylate (240 g) and pyridine (240 g), and treated in the same manner as in Example 1 to give the following pyrophosphate (445 g):

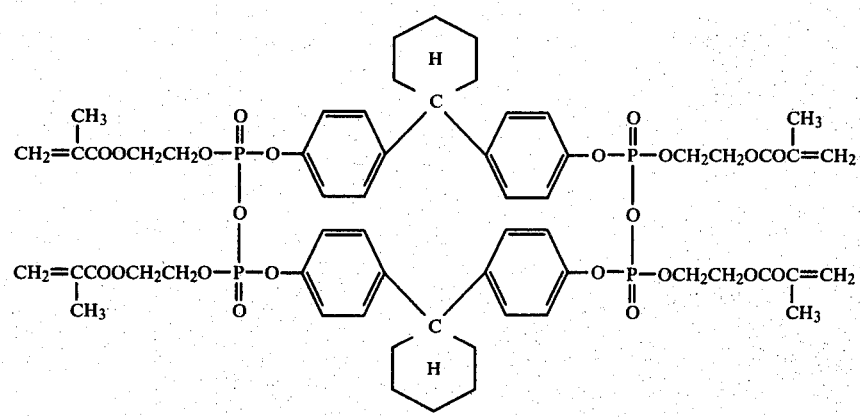

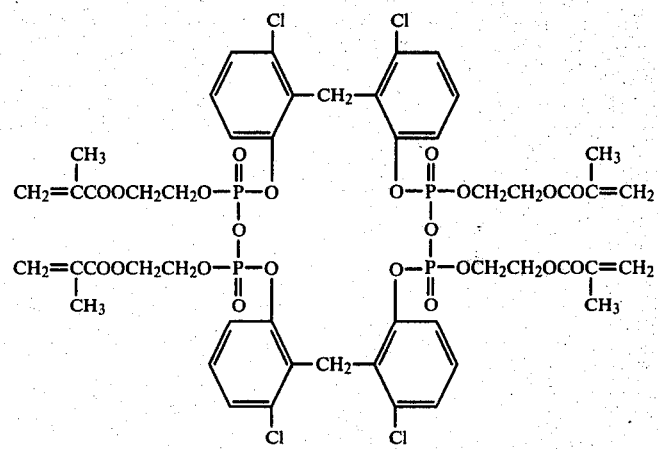

IR: $\nu_{max}$ cm$^{-1}$
2950, 1720, 1630, 1600, 1365, 1295, 980, 845
NMR(CDCl$_3$): δ
  7.3 (m, 3H×4, arom. protons)
  6.10 (bs, 1H×4, vinyl proton)
  5.55 (m, 1H×4, vinyl proton)
  4.25 (m, 4H×4, —CH$_2$CH$_2$—)
  3.80 (s, 2H×2, —CH$_2$—)
  1.90 (d, 3H×4, vinyl CH$_3$)

IR: $\nu_{max}$ cm$^{-1}$
2900, 1720, 1630, 1600, 1365, 1295, 985
NMR(CDCl$_3$): δ
  7.15 (ABq, 4H×4, arom. protons)
  6.10 (bs. 1H×4, vinyl proton)
  5.55 (m, 1H×4, vinyl proton)
  4.25 (m, 4H×4, —CH$_2$CH$_2$—)
  1.90 (d, 3H×4, vinyl CH$_3$)
  1.40 (m, 10H×2, —(CH$_2$)$_5$—)

EXAMPLE 6

Bis(4-hydroxyphenyl)cyclohexane (268 g), phosphoryl chloride (320 g) and calcium chloride (50 g) were reacted in the same manner as shown in Example 1 to give the following phosphoryl dichloride (480 g):

EXAMPLE 7

Bis(4-hydroxyphenyl)sulfone (250 g), phosphoryl chloride (320 g) and calcium chloride (50 g) were reacted in the same manner as shown in Example 1 to give the following phosphoryl dichloride (464 g):

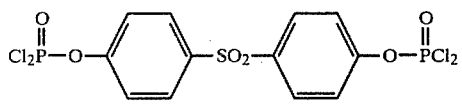

The phorphoryl dichloride was reacted with 2-hydroxyethyl methacrylate (240 g) and pyridine (240 g), and treated in the same manner as in Example 1 to give the pyrophosphate (512 g):

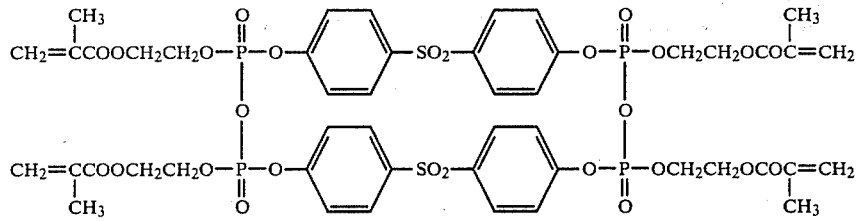

IR: $\nu_{max}'$cm$^{-1}$
2950, 1720, 1630, 1600, 1365, 1330, 1130, 980
NMR(CDCl$_3$): δ
7.30 (ABq, 4H×4, arom. protons)
6.10 (bs, 1H×4, vinyl proton)
5.55 (m, 1H×4, vinyl proton)
4.25 (m, 4H×4, —CH$_2$CH$_2$—)
1.90 (d, 3H×4, —CH$_3$)

EXAMPLE 8

Bis(4-hydroxyphenyl)ether (202 g), phosphoryl chloride (320 g) and calcium chloride (50 g) were reacted in the same manner as shown in Example 1 to give the following phosphoryl dichloride (416 g):

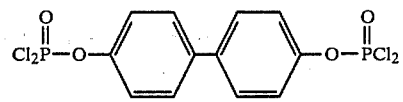

The phosphoryl dichloride was reacted with allyl alcohol (110 g) and pyridine (240 g), and treated in the same manner as in Example 1 to give the following pyrophosphate (308 g):

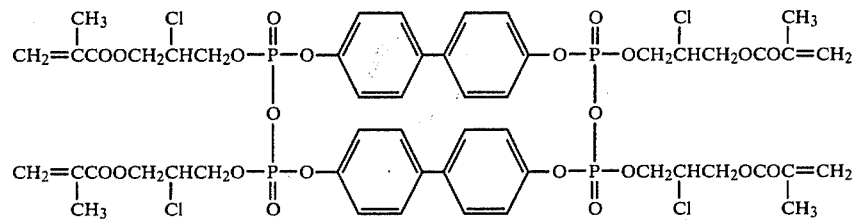

IR: $\nu_{max}'$cm$^{-1}$
2900, 1630, 1600, 1365, 1295, 1100, 980
NMR (CDCl$_3$): δ
7.10 (ABq, 4H×4, arom. protons)
5.60 (m, 2H×4, vinyl protons)
4.10 (bs, 1H×4, vinyl proton)
3.50 (t, 2H×4, —CH$_2$—)

EXAMPLE 9

4,4'-dihydroxy biphenyl (29 g), phosphoryl chloride (32 g) and calcium chloride (5 g) were reacted in the same manner as shown in Example 1 to give the following phosphoryl dichloride (50 g):

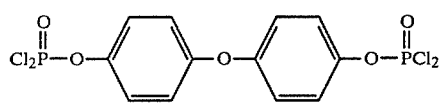

The phosphoryl dichloride was reacted with 2-chloro-3-hydroxypropyl methacrylate (33 g) and pyridine (24 g), and treated in the same manner as in Example 1 to give the pyrophosphate (25.5 g):

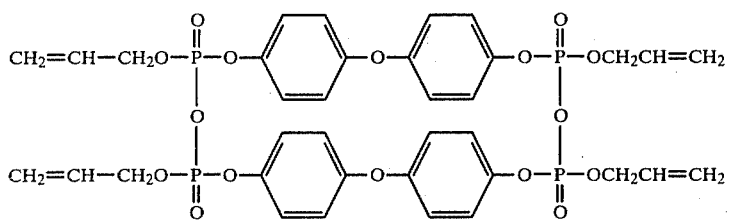

IR: $\nu_{max}'$cm$^{-1}$
2950, 1720, 1630, 1600, 1370, 1160, 1000, 760
NMR(CDCl$_3$): δ
7.2 (ABq, 4H×4, arom. protons)
6.10 (bs, 1H×4, vinyl proton)
5.55 (m, 1H×4, vinyl proton)
4.20 (m, 4H×4, —C$\underline{H}_2$—CH(Cl)—C$\underline{H}_2$)
3.65 (m, 1H×4, —CH$_2$C$\underline{H}$(Cl)CH$_2$—)
1.90 (d, 3H×4, vinyl CH$_3$)

EXAMPLE 10

A fused-quartz powder was ground in a ballmill to obtain a particle size under 200 mesh.

To a solution of sodium hydroxide (pH 9.0–9.8), 0.5 wt% of γ-methacryloxypropyl trimethoxy silane and the quartz powder were added and mixed well with stirring to give a mushy paste, which was then dried at 130° C. to obtain a silane-coupled quartz powder.

The pyrophosphate (70 wt%) which was prepared by the procedure in Example 1 was combined with ethylene glycol dimethacrylate (30 wt%) to obtain the resin binder. The binder (20 wt%) and the silane coupled quartz powder 80 wt%) were mixed well to provide a paste.

The paste was divided into two parts, one of which was mixed with 0.6 wt% of N,N'-dimethyl-p-toluidine to give a uniform dispersion, and to the other was added 0.8 wt% of benzoyl peroxide. Equal amounts of the two dispersions were mixed and scoured to provide the composite resin. The handling characters and physical properties were examined.

The results are shown in the following table:

| Examination Item*[I] | Result | S.D.*[IV] |
|---|---|---|
| Gel time (min.) | 2.5 | 0.35 |
| Hardening time (min.) | 4.5 | 0.45 |
| Diametral tensile strength (MPa) | 50.1 | 2.9 |
| Compressive strength (MPa) | 314.3 | 18.6 |
| Transverse strength (MPa)*[II] | 106.4 | 5.0 |
| Modulus of elasticity (MPa) × $10^2$*[III] | 214.3 | 5.1 |
| Thermal dimensional change (cm/cm/°C.) × $10^{-6}$ | 36.2 | 0.1 |
| Rockwell hardness ($H_RH$) | 114 | 0.5 |
| Knoop hardness (50g, 5 sec.) | 86 | 3 |
| Water sorption (mg/cm$^2$) | 0.41 | 0.05 |

*[I]According to American Dental Association Specification No. 27
*[II]According to International Organization for Standardization ISO-4049.
*[III]Calculated according to Japanese Industrial Standard JIS K-6705.
*[IV]Estimated standard deviation of 5 test pieces

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A cyclic pyrophosphate derivative having the formula (I):

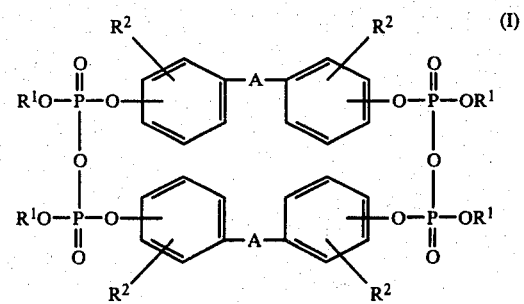

wherein A represents a direct bond between the two phenyl rings or a divalent moiety selected from the group consisting of lower alkylene, aryl substituted lower alkylene, cycloalkylidene, sulfonyl and oxy;

$R^1$ represents allyl, acryloyloxy lower alkyl or methacryloxy lower alkyl, in which the lower alkyl can be substituted with halogen; and $R^2$ represents independently hydrogen, halogen, lower alkyl or lower alkoxy.

2. The cyclic pyrophosphate according to claim 1, wherein A is a direct bond between the two penyl rings.
3. The cyclic pyrophosphate according to claim 1, wherein A is dimethyl methylene.
4. The cyclic pyrophosphate according to claim 1, wherein A is phenyl methylene.
5. The cyclic pyrophosphate according to claim 1, wherein A is sulfonyl.
6. The cyclic pyrophosphate according to claim 1, wherein A is oxy.
7. The cyclic pyrophosphate according to claim 1, wherein A is cyclohexylidene.
8. The cyclic pyrophosphate according to claim 1, wherein every $R^2$ is hydrogen.
9. The cyclic pyrophosphate according to claim 1, wherein two of the $R^2$ groups are halogen.
10. The cyclic pyrophosphate according to claim 1, wherein every $R^2$ is halogen.
11. The cyclic pyropshophate according to claim 1, wherein $R^1$ is allyl.
12. The cyclic pyrophosphate according to claim 1, wherein $R^1$ is 2-methacryloyloxy ethyl.
13. The cyclic pyrophosphate according to claim 1, wherein $R^1$ is 1-methyl-2-methacryloyloxy ethyl.
14. The cyclic pyrophosphate according to claim 1, wherein $R^1$ is 2-halo-3-methacryloyloxy ethyl.
15. The cyclic pyrophosphate according to claim 1, wherein $R^1$ is acryloyloxy ethyl.
16. A process for the production of cyclic pyrophosphate derivatives having the formula (I)

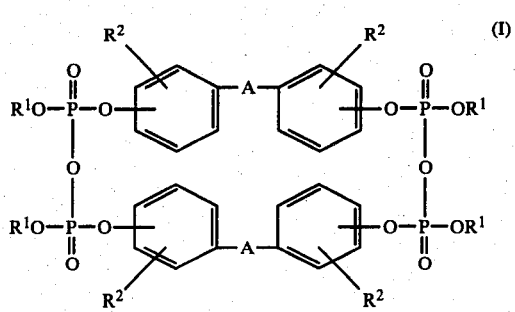

wherein A represents a direct bond between the two phenyl rings or a divalent moiety selected from the group consisting of lower alkylene, aryl substituted lower alkylene, cycloalkylidene, sulfonyl and oxy;

$R^1$ represents allyl, acryloyloxy lower alkyl or methacryloyloxy lower alkyl, in which the lower alkyl can be substituted with halogen; and $R^2$ represents independently hydrogen, halogen, lower alkyl or lower alkoxy;

the process comprising:

reacting, under anhydrous conditions, a phenol derivative having the formula (II)

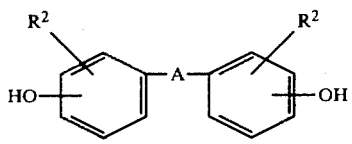

(II)

with a phosphoryl halide to give the phosphoryl dihalide derivative having the formula (III)

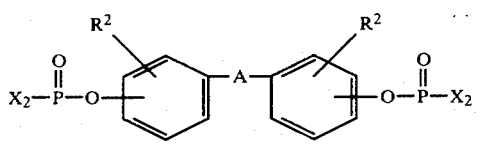

(III)

wherein X is halogen;

adding to the phosphoryl dihalide derivative having the formula (III), under anhydrous conditions, an alcohol having the formula $R^1$—OH to obtain a phosphoryl halide derivative having the formula (IV)

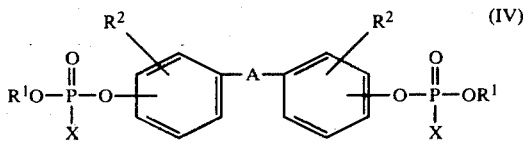

(IV)

which is then hydrolyzed, in the presence of a base, to provide the cyclic pyrophosphate derivative having the formula (I).

17. The process according to claim 16, wherein the base, present during hydrolysis, is an amine.

* * * * *